United States Patent [19]

Pozzi

[11] Patent Number: 5,257,931
[45] Date of Patent: * Nov. 2, 1993

[54] DENTAL TOOTH SHADE/HUE MATCHING REFERENCE SYSTEM

[75] Inventor: Bruno Pozzi, Camarillo, Calif.

[73] Assignee: American Tooth Industries, Oxnard, Calif.

[*] Notice: The portion of the term of this patent subsequent to Nov. 19, 2008 has been disclaimed.

[21] Appl. No.: 791,155

[22] Filed: Nov. 13, 1991

Related U.S. Application Data

[63] Continuation-in-part of Ser. No. 686,809, Apr. 17, 1991, Pat. No. 5,066,227.

[51] Int. Cl.⁵ .......................................... A61C 19/10
[52] U.S. Cl. ............................... 433/26; 206/83
[58] Field of Search ............................. 433/26; 206/83

[56] References Cited

U.S. PATENT DOCUMENTS

| | | | |
|---|---|---|---|
| 1,423,921 | 7/1922 | Duffy | 206/83 |
| 1,709,066 | 4/1929 | Field | 433/26 |
| 2,184,977 | 12/1939 | Martin | 206/83 |
| 2,805,478 | 9/1957 | Adams | 433/26 |
| 4,115,922 | 9/1978 | Alderman | 433/26 |
| 4,541,801 | 9/1985 | Mackert et al. | 433/26 |

*Primary Examiner*—John J. Wilson
*Attorney, Agent, or Firm*—Emrich & Dithmar

[57] ABSTRACT

A system for providing artificial teeth with life-like shade and hue, or for matching the shade and hue of an artificial tooth with the shade and hue of one's natural teeth, employs a double-sided master shade guide and a plurality of paired sample teeth, with each pair having a given shade and hue corresponding to a tooth on the master shade guide and attached to a holder. One side of the master shade guide includes a first set of reference teeth arranged by shade, while a second set of reference teeth arranged by hue and visually isolated from the first set are disposed on a second, opposed side of the shade guide. A support base, or carrier, is adapted to receive and support the master shade guide and the paired sample teeth holders. The carrier includes a plurality of spaced compartments, each receiving and supporting a plurality of paired sample teeth holders. All pairs of sample teeth in a given compartment are of the same shade and hue. The various compartments contain pairs of sample teeth covering the full range of shade and hue found on the master shade guide. One sample tooth is removably attached to its associated holder, while the other paired sample tooth remains with the holder. The holder is adapted to receive patient indicia as is the removable sample tooth allowing one sample tooth to be sent to a laboratory for fabrication of an appliance, while permitting the dentist to retain the matched sample tooth for his records and for verification of the fabricated appliance.

47 Claims, 2 Drawing Sheets

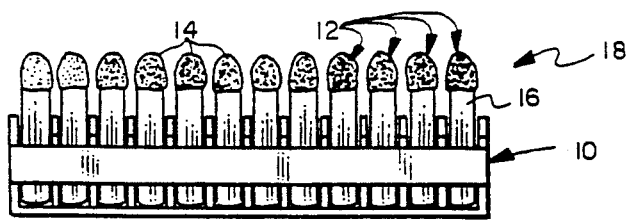
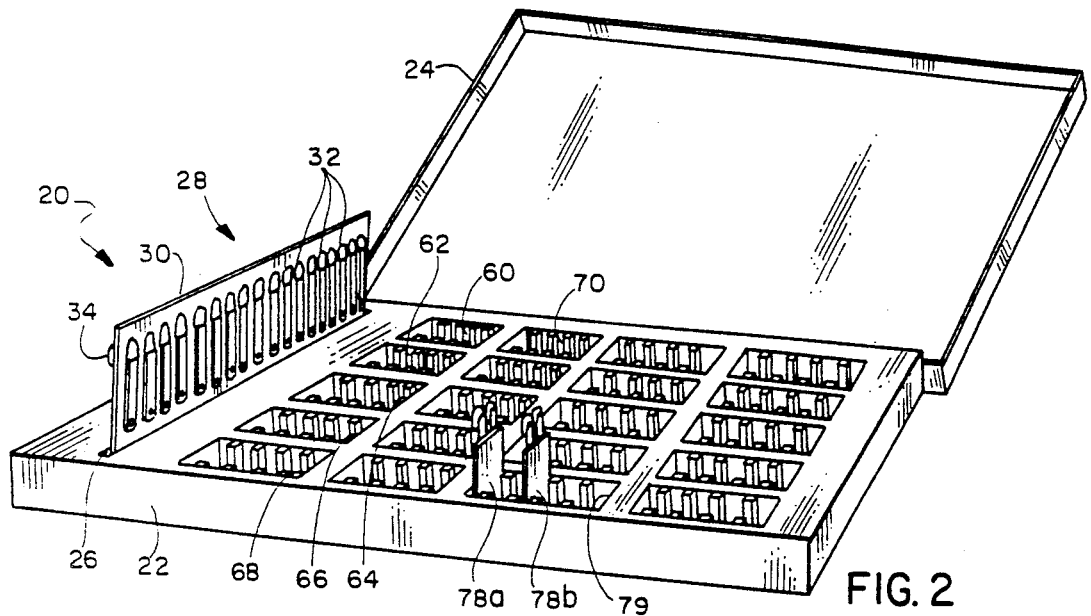
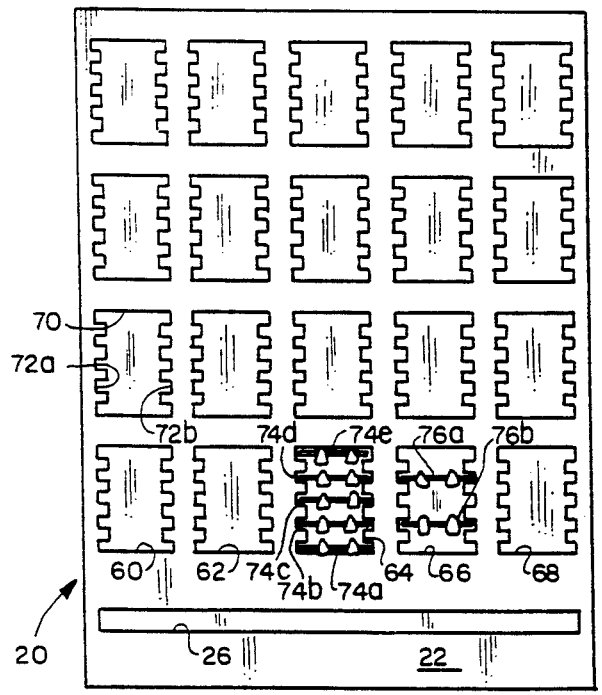
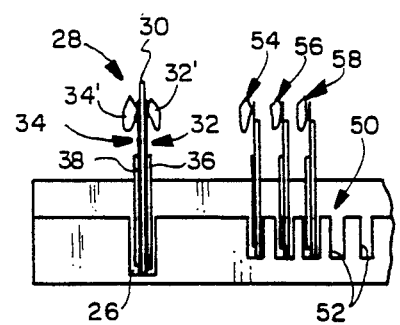

5,257,931

DENTAL TOOTH SHADE/HUE MATCHING REFERENCE SYSTEM

RELATED APPLICATION

This is a continuation-in-part of application Ser. No. 686,809, filed Apr. 17, 1991, in the name of the present inventor for DENTAL TOOTH SHADE MATCHING SYSTEM, now U.S. Pat. No. 5,066,227.

FIELD OF THE INVENTION

This invention relates generally to the fabrication of denture appliances and is particularly directed to an improved system for providing artificial teeth with a life-like color and shade.

BACKGROUND OF THE INVENTION

Dental appliances such as false teeth and bridges have become more commonplace as the number of senior citizens increases, as such appliances become more affordable, and as concern with personal appearance increases. The fabrication of dental appliances by either a dentist or technician has been simplified with the advent of plastic teeth, while bridge supports have facilitated the accurate reconstruction of teeth configurations. While the structural integrity and useful lifetime of such dental appliances are of the utmost importance, the appearance and aesthetics of such structures are also of considerable importance to most users and potential users. Increasingly the cost and time involved in reconstructing a patient's teeth are devoted to aesthetics considerations such as the color, shade and other characteristics of the artificial teeth in the dental appliance. The goal is, of course, to match the newly installed artificial teeth in shade and hue as closely as possible with the patient's remaining teeth and to provide a most natural appearance for the user. It is also desirable, once the proper hue is determined to provide a progressively darker shade in the same hue, where multiple teeth are needed and the replacement teeth are to be located toward the rear of the mouth.

The dentist's first task is to prepare the patient's mouth in order to fabricate the dental appliance, commonly referred to as "dentures" such as a partial, a crown, a bridge, veneers, laminates, or over dentures. With the patient's mouth prepared, an impression of the patient's mouth is then obtained. The dentist must then determine the shade and color, or hue, of any artificial teeth in the dental appliance.

Shade matching or shade progression is generally accomplished by means of a shade guide 18 such as shown in FIG. 1. A typical prior art shade guide 18 includes an elongated, linear holder 10 containing a plurality of specimens 12. Each of the specimens is comprised of a sample tooth 14 and a support member 16 for attaching the sample tooth to the holder 10. Each sample tooth 14 is provided with a predetermined shade and hue for matching with the patient's natural teeth. Shade guides are typically provided by manufacturers of prefabricated teeth for use as dentures, partials and implants over dentures. Crowns, bridges, laminates and veneers are, on the other hand, generally manufactured by dental laboratories using tooth powder materials (resins or porcelain) which have also been fabricated by tooth manufacturers.

The conventional prior art shade guide 18 such as shown in FIG. 1 includes an average of twelve shade selections fixedly mounted in sequence on the common holder The dentist must match one of these shades to the shade of existing teeth in the patient's mouth. If the patient is edentulous, the dentist, together with the patient, typically selects a hue and shade progression according to the age of the patient based upon the dentist's experience with the patient's approval. Once a hue and shade progression are selected, the doctor records the shade numbers and/or brand of teeth or material on a prescription. The prescription together with the patient's impression, which is usually comprised of hydrocolloid, silicone, alginate or rubber base, are sent to a laboratory for fabrication of a dental appliance. The laboratory set-up man or master technician selects the teeth for dentures, partials or implant over dentures, or the tooth materials for crowns, bridges, laminates or veneers by matching the shade number provided by the dentist in the prescription.

Although in widespread use, this approach is not error-proof, nor does it guarantee a perfect match for several reasons. For example, the shade guide used by the dentist is not the same as that used by the laboratory. The shade and hue of the materials used in a shade guide change with time, e.g., color intensity is reduced and colors tend to lighten, or fade, over time. This is particularly true where the shade guide is overexposed to sunlight or frequently disinfected, or sterilized, resulting in a change in the original tones. In addition, the doctor or fabricating technician may misread the color number on the shade guide or the shade guide manufacturer may erroneously identify the shade of one or more specimens in the shade guide. Finally, the tooth manufacturer may slightly change the shades of teeth or tooth powder in its production batches because of changes, which frequently depend on availability, of one or more ingredients. The occurrence of any of these events will result in an inaccurate matching of artificial teeth shade with the shade of natural teeth because the technician normally does not have access to the patient and was not present at the initial shade selection by the dentist.

While most mechanical problems with dental appliances can be corrected at chair side, the problems of shade matching discussed above cannot generally be thus corrected and typically require a return of the dental appliance to the denture manufacturer or lab resulting in patient inconvenience and dentist loss of labor time.

The present invention addresses the aforementioned problems of the prior art by providing an improved dental tooth shade matching reference system which provides the dentist as well as the tooth fabricating technician with a specimen precisely matched in shade and hue with the patient's natural teeth. Patient identifying labels are provided on both the dentist's and technician's specimens to eliminate the possibility of identification errors. This arrangement ensures that the patient's reference shade and hue are precisely known (1) at the time of patient examination by the dentist, (2) when the artificial tooth is fabricated, and (3) when the dental appliance is delivered to the dentist for installation in a patient.

OBJECTS AND SUMMARY OF THE INVENTION

Accordingly, it is an object of the present invention to provide an improved arrangement for matching artificial denture appliances with life-like shades and colors, or hues.

It is another object of the present invention to provide a shade and hue reference system for matching the shade and hue of an artificial denture with a desired life-like shade and hue in a foolproof arrangement which allows for verification of the artificial denture shade and hue prior to installation.

Yet another object of the present invention is to attach a patient's identifying information to a holder to which a first denture sample having a given hue and color is permanently attached, while allowing a second denture sample with matching hue and color and also having patient identifying data to be removed from the holder for transport to a denture manufacturer which permits verification of fabricated denture hue and color and eliminates the possibility of error or confusion in matching denture hue and color for a given patient.

A further object of the present invention is to provide a self-contained reference system for matching the shade of a dental appliance with a desired life-like color which can be re-used without limit.

A still further object of the present invention is to provide an improved dental tooth shade matching reference system which essentially eliminates the possibility of shade mismatches arising from mistake such as of the patient's specimen or identity and allows for precise matching of virtually any shade and hue.

These objects of the present invention are achieved and the disadvantages of the prior art are eliminated by a dental tooth shade/hue matching reference system for matching the shade/hue of artificial teeth with the shade/hue of a patient's natural teeth or for providing artificial teeth with a life-like shade/hue, the system comprising: a shade/hue unit having a shade/hue of a patient's natural teeth or having a life-like shade/hue, wherein the shade/hue unit includes: a holder; and first and second shade/hue specimen teeth each having the same shade/hue, wherein at least one of the shade/hue specimen teeth is removably attached to the holder, and wherein the holder includes shade/hue identifying data and patient identification area.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIG. 1 is an elevation view of a prior art dental tooth shade guide;

FIG. 2 is a perspective view of a dental tooth shade/hue matching reference system in accordance with the principles of the present invention;

FIG. 3 is a plan view of the inventive dental tooth shade/hue matching reference system shown in FIG. 2;

FIG. 4 is a partial lateral sectional view of the dental tooth shade/hue matching reference system shown in FIG. 3;

DETAILED DESCRIPTION OF THE PREFERRED EMBODIMENTS

Figure 5A:
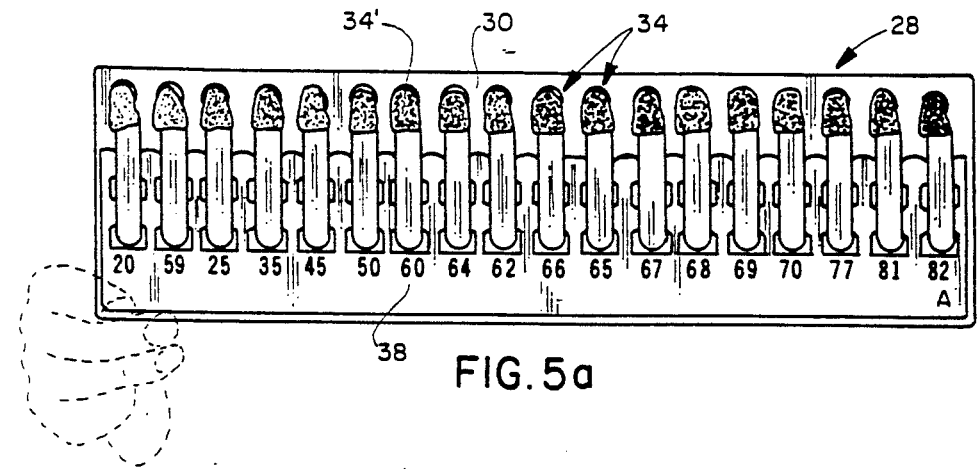
FIGS. 5a and 5b are respectively front and rear elevation views of a reference master shade/hue guide for use in the shade/hue matching reference system of the present invention.

Referring to FIG. 2, there is shown a perspective view of a dental tooth shade/hue matching reference system 20 in accordance with the principles of the present invention. A plan view of the shade/hue matching reference system 20 with cover removed is shown in FIG. 3. The shade/hue matching reference system 20 includes a generally rectangular base or carrier 22 having a removable or hinged cover 24. Base 22 includes a plurality of spaced, generally rectangular bins, or sample compartments, some of which are identified in FIGS. 2 and 3 as elements 60, 62, 64, 66, 68 and 70. Each of the bins includes a plurality of pairs of spaced recessed edge portions 72a, 72b as shown for bin 70 in FIG. 3. Each pair of aligned, recessed edge portions 72a, 72b for each of the bins in base 22 is adapted to receive and support a respective shade/hue unit. As shown in FIG. 3, bin 64 has positioned therein and provides support for five shade/hue units 74a–74e. Bin 66 is shown holding two such shade/hue units 76a and 76b. Each of the aforementioned shade/hue units is easily inserted in and removed from a respective bin by sliding it vertically. The bins provide support for and maintain the shade/hue units in a generally vertical orientation as shown for shade/hue units 78a and 78b in bin 79 in FIG. 2.

Figure 5B:
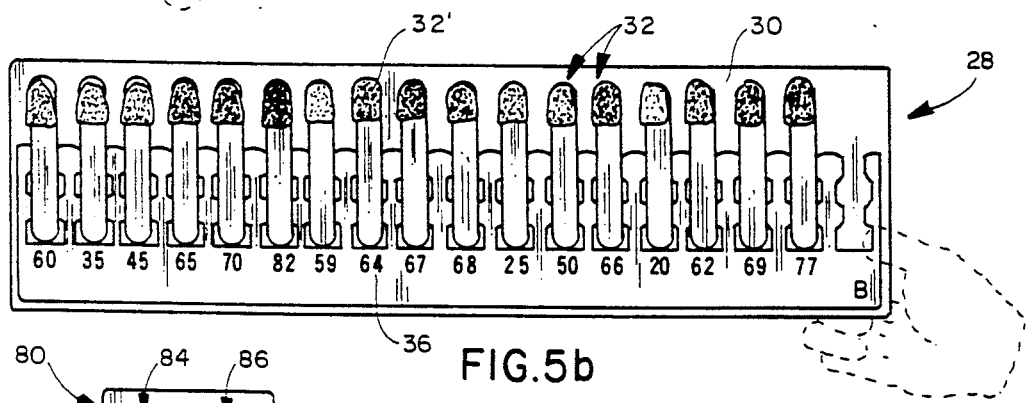

Base 22 further includes an elongated, generally linear shade/hue guide slot 26 adapted to receive and provide support for a reference master shade/hue guide 28. FIGS. 5a and 5b respectively show front and rear elevation views of the reference master shade/hue guide 28. The reference master shade/hue guide 28 includes a generally flat, elongated shade/hue guide panel 30 having on a first side a first set of shade/hue guide units 32 and on a second, opposed side a second set of shade/hue guide units 34. Each of the first and second shade/hue guide units 32, 34 includes a respective specimen tooth 32', 34' as also shown in the partial lateral sectional view of FIG. 4. Each of the shade/hue guide units 32, 34 further includes a respective support arm 36, 38 which is attached to an associated specimen tooth and provides support therefore. The specimen teeth 32' of the first set of shade/hue guide units 32 may be arranged in accordance with the shade of each of the specimen teeth. Similarly, the second set of shade/hue guide units 34 may be arranged on the second surface of the shade/hue guide panel 30 in accordance with the hue of the specimen teeth. The shades of the specimen teeth in the first and second sets are the same, but the sequence is different on each side of panel 30 creating an illusion that the shade guides are different.

As shown in FIGS. 5a and 5b, each of the support arms 36, 38 to which a respective specimen tooth 32', 34' is attached is also removably held by insertion into a receptacle such as designated 31 in FIG. 5b. The receptacles 31 are formed as recesses in the panel 30 with opposed inward projections 31a engaging and holding the support arm or tab 36 in a snap-fit.

In an alternate embodiment not illustrated, the support arms 36, 38 may be removably attached to the shade/hue guide panel 30 by means of an aperture in the bottom of the tab or arm and a mounting stud formed in the panel 30. A plurality of mounting studs are arranged in a spaced manner on opposing surfaces of the shade/hue guide panel 30 to allow for the first and second shade/hue guide units 32, 34 to be attached to or removed from the shade/hue guide panel. It will be observed, and it is considered an important feature of the inventive master shade guide, that the panel 30 extends above the sample teeth when they are received in their associated receptacles. This provides visual isolation by displaying the tooth on a uniform field (the panel may be blue, high density gray or white) and permits the user to concentrate his or her faculties on that particular shade or hue.

Ease in removal of each of the shade/hue guide units 32, 34 allows the shade/hue guide units to be replaced by a new one after an extended period of time of use to avoid discoloration of the specimen teeth 32', 34' which leads to inaccurate shade/hue matching with natural teeth. FIG. 5a shows the specimen teeth 34' arranged by shade from left to right in proceeding from light to dark shades. FIG. 5b shows the specimen teeth 32' arranged in groups by hue from left to right, with the specimen teeth varying in shade from light to dark in proceeding from left to right within each group. The facing surfaces of the shade/hue guide panel 30 are provided with a solid color for a viewing background for the specimen teeth, which color in a preferred embodiment is blue or neutral density gray.

As shown in the partial sectional view of FIG. 4, bin 50 includes a plurality of spaced slots 52 each aligned with a pair of the aforementioned facing recessed edge portions within the bin for receiving a respective shade/hue unit, as shown for shade/hue units 54, 56 and 58 in the figure. As shown in the figures, when the shade/hue matching reference system 20 is in use, the reference master shade/hue guide 28 is maintained in a generally vertical orientation as are the various shade/hue units for ease of viewing by the dentist. When not in use, the reference master shade/hue guide 28 as well as the various shade/hue units may be removed from their respective support slots and either placed in a sample bin or laid flat on an upper surface of the base 22 to allow the cover 24 to be positioned on the base in a manner which protects and retains the reference master shade/hue guide as well as the various shade/hue units. In a preferred embodiment, two of the sample bins may be used to accommodate a plurality of shade/hue units adapted for providing dental appliances having custom-made dentures with one's individual shade and hue as described below.

Figure 6:
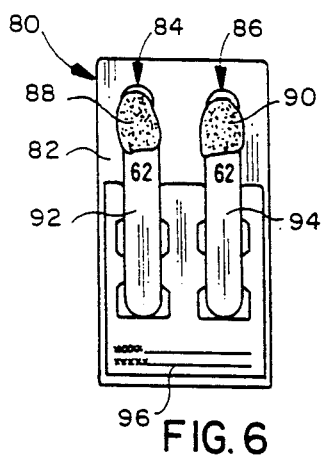
FIG. 6 is an elevation view of one embodiment of a tooth shade unit for use in the dental tooth shade/hue matching reference system of the present invention.

Referring to FIG. 6, there is shown an elevation view of a preferred embodiment of a shade/hue unit 80 for use in the present invention. Shade/hue unit 80 includes a holder, or base, 82 upon which a patient data record 96 may be entered. Attached to holder 82 are first and second shade/hue specimens 84 and 86. The holder 82 is also preferably a solid color, such as white, blue or neutral gray, forming a suitable background for viewing the first and second specimens 84, 86. Holder 82 extends above the first and second shade/hue specimens 84, 86 to highlight their shade and hue and facilitate focusing the viewer's attention on these specimens. The first shade/hue specimen 84 includes a first sample tooth 88 attached to a first end of a first handle 92. Similarly, the second shade/hue specimen 86 includes a second sample tooth 90 attached to a first end of a second handle 94. Each of the handles 92, 94 is inserted in a respective receptacle within holder 82 and is frictionally retained therein by means of a respective pair of spaced inward projections 91a, 91b and 93a, 93b. The first and second sample teeth 88, 90 are provided with the same shade and hue, with the appropriate shade/hue information disposed on the first and second handles 92, 94. Corresponding shade/hue data is also entered on the holder 82 as shown in the figure. One of the shade/hue specimens is permanently attached to holder 82, while the other shade/hue specimen is removable from the holder for shipment to the denture manufacturer or lab. Thus, in one embodiment, an epoxy cement 102, or other conventional adhesive material, may be used to fixedly attach first handle 92 to holder 82. Second handle 94 of the second shade/hue specimen 86 may be removed from the receptacle in holder 82. Once removed, the second specimen 86 may be shipped to a remote denture manufacturer or lab with the shade of the thus produced artificial tooth capable of accurate verification when received by the dentist prior to installation using the holder-mounted first shade/hue specimen 84.

Figure 7:
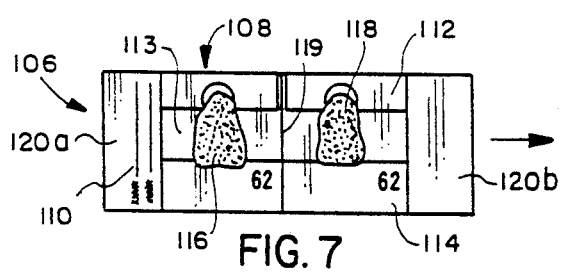
FIG. 7 is an elevation view of another embodiment of a tooth shade/hue unit for use in the dental tooth shade/hue matching reference system of the present invention.

Referring to FIG. 7, there is shown an elevation view of another embodiment of a tooth shade/hue unit 106 for use in the dental tooth shade/hue matching reference system of the present invention. Shade/hue unit 106 includes a holder 108 comprised of an upper brace 112, a lower brace 114, and first and second end braces 120a, 120b connecting the upper and lower braces. A center brace 119 also connects the upper and lower braces 112, 114. The upper and lower braces 112, 114 are disposed forward of the first and second end braces 120a, 120b, with an inter-brace space 113 disposed intermediate the upper and lower braces. First and second sample teeth 116 and 118 are adapted for sliding insertion within the inter-brace space 113 between the upper and lower braces 112, 114. A tab on the rear of each of the first and second sample teeth 116, 118 allows the sample teeth to be inserted in the inter-brace space 113 and maintained therein by engagement of the tab by the upper and lower braces 112, 114. The rear tabs on each of the first and second sample teeth 116, 118 are not shown in the figure for simplicity. The first end brace 120a is adapted to receive patient indicia and further includes shade/hue information. Similarly, adjacent spaces on the lower brace 114 adjacent the first and second sample teeth 116, 118 include shade/hue data characteristic of the shade and hue of the first and second sample teeth 116, 118. As in the previously discussed shade/hue unit, the shade and hue of each of the first and second sample teeth 116, 118 are identical. The first sample tooth 116 may be permanently mounted in the holder 108 by conventional means such as by an epoxy cement, while the second sample tooth 118 may be removed from the holder 108 in the direction of the arrow and shipped to a denture manufacturer or lab. Upon its return, the shade and hue of the manufactured denture may be compared with that of the first sample tooth 116 for verifying the shade and hue of the artificial tooth in accordance with the present invention.

Figure 8A:
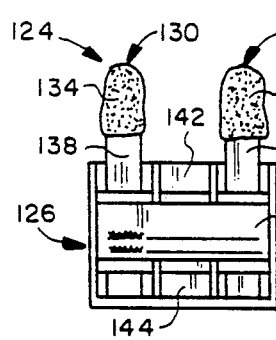
FIGS. 8a and 8b are respectively front and rear elevation views of yet another embodiment of a tooth shade/hue unit for use in the present invention.
Figure 8B:
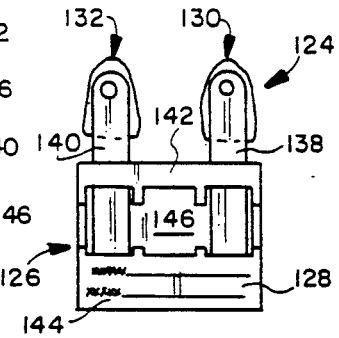

Referring to FIGS. 8a and 8b, there are respectively shown front and rear elevation views of yet another shade/hue unit 124 for use in the dental tooth shade/hue matching reference system of the present invention. Shade/hue unit 124 includes a holder 126 comprised of an upper brace 142, a lower brace 144, and an intermediate brace 146. Disposed on the intermediate brace 146 is sample tooth shade/hue information as well as a space to enter patient indicia. Similarly, disposed on an opposed surface of the lower brace 144 is a location for the entry of patient indicia 128. Inserted in holder 126 are first and second shade/hue specimens 130 and 132. The first shade/hue specimen 130 includes a first sample tooth 134 attached to one end of a first support arm or tab 138. Similarly, the second shade/hue specimen 132 includes a second sample tooth 136 attached to a first end of a second tab 140. Respective second ends of the first and second tabs 138, 140 are adapted to engage a lower portion of the holder 126. The second, or lower, end of the first tab 138 is fixedly attached to the holder 126 by conventional means such as an epoxy cement, which is not shown for simplicity. Other conventional means may be employed for permanently attaching the first tab 138 to holder 126. The lower end of the second tab 140 is provided with a locking tab for engaging a lower portion of the holder 126 in a removable manner which permits insertion into and retraction from the holder 126 of the second shade/hue specimen 132. Other conventional means well known to those skilled in the relevant arts may be employed for removably attaching the second tab 140 to holder 126, although these are not shown for simplicity. Each of the first and second tabs 138, 140 includes on the surface thereof, shade/hue information relating to the shade and hue of the two sample teeth 134, 136 which are identical for both teeth. In this manner, the second sample tooth 136 may be removed from the holder 126 and shipped to an denture manufacturer or lab having the correct shade/hue information imprinted thereon, while the dentist treating the patient retains the holder 126 and the first sample tooth 134 having patient indicia as well as relevant shade/hue information. This permits verification of the shade and hue of the thus manufactured appliance when received by the dentist.

Figure 9A:
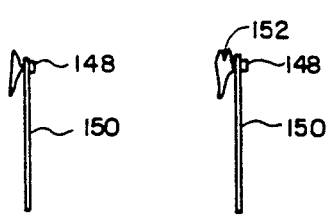
FIGS. 9a and 9b are elevation views of a tooth specimen and supporting handle for use in fabricating an artificial tooth having a custom-made shade and hue respectively showing the specimen tab before and after applying the artificial tooth material.
Figure 9B:
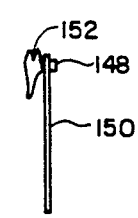

Referring to FIGS. 9a and 9b, there are shown elevation views of a tab 148 and a supporting handle 150 for use in fabricating an artificial tooth having a custom-made shade and hue respectively showing the specimen tab before and after applying the artificial tooth material. Tab 148 is used as a base, or foundation, for building up the tooth specimen 152. The tooth specimen is matched in hue and color with the patient's real teeth, or to provide a life-like shade and hue. The tooth specimen 152 is also shaped as desired and may be formed from composite materials or a cold cure colored powder. Tab 148 is attached to the support handle 150 to facilitate forming the artificial tooth specimen 152 and for subsequent transport to a denture manufacturer or lab.

There has thus been shown an improved dental tooth shade/hue matching reference system for providing artificial teeth with a life-like shade and hue, or for matching the shade and hue of an artificial tooth with the shade and hue of one's natural teeth. The shade matching reference system employs a double-sided shade guide having two groups of sample teeth, with one group arranged according to shade and the other group arranged according to hue in the guide. The system further includes a plurality of sample teeth holders, each having a pair of sample teeth with the same shade and hue attached thereto. One of the sample teeth may be permanently secured to the holder, while the second sample tooth can be removed from the holder and shipped to a denture manufacturer or lab. The second sample tooth as well as the combination of the first sample tooth and holder include shade and hue information, while the first sample tooth and holder combination are adapted to receive patient indicia to allow the dentist to verify artificial tooth shade and hue prior to installation. The inventive reference system essentially eliminates the possibility of errors in patient identification as well as shade and hue mismatches.

While particular embodiments of the present invention have been shown and described, it will be obvious to those skilled in the art that changes and modifications may be made without departing from the invention in its broader aspects. For example, the shade/hue matching reference system may be used for only matching artificial tooth shade or for only matching artificial tooth hue. Similarly, the system may be used with the combination of a shade/hue reference master guide in combination with a plurality of shade/hue specimen teeth units each having a different shade and hue, or may be used only with the shade/hue reference master guide or only with the plurality of different shade/hue specimen teeth units in matching the shade/hue of artificial teeth with the shade/hue of a patient's natural teeth or for providing artificial teeth with a life-like shade and hue. In addition, while some of the specimen teeth are disclosed as attached to a holder by means of a mounting stud inserted through an aperture in a handle, various other mounting arrangements well known to those skilled in the relevant arts could as easily be employed. For example, the handle may be sized to engage tabs on the holder in a tight-fitting manner to allow for frictional retention of the handle and the specimen tooth attached thereto. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

I claim:

1. A dental tooth shade and hue matching reference system for matching the shade and hue of artificial teeth with the shade and hue of a patient's natural teeth or for providing artificial teeth with a life-like shade and hue, said system comprising:

a shade and hue unit having a shade and hue of a patient's natural teeth or having a lifelike shade and hue, wherein said shade and hue unit includes:
   a holder; and
   first and second shade and hue specimen teeth each having the same shade and hue, wherein at least one of said shade and hue specimen teeth includes a support arm said to be easily handled by a thumb and forefinger grip of a user and removably attached to said holder, and characterized in that said holder includes shade and hue identifying data for said specimen teeth and a patient identification area, and said support arm of said removable specimen tooth includes shade and hue identifying data.

2. The system of claim 1 further comprising a plurality of shade and hue units, wherein each shade and hue unit includes respective first and second shade and hue specimen teeth having the same shade and hue, and wherein the shade and hue of the specimen teeth of each shade and hue unit vary over a range of shades and hues.

3. The system of claim 2 wherein each holder comprises a generally flat panel adapted to receive and support a respective pair or first and second shade and hue specimen teeth.

4. The system of claim 3 wherein each holder includes mounting means for removably coupling at least one of said shade and hue specimen teeth to said holder.

5. The system of claim 4 wherein each mounting means couples at least one of said shade and hue specimen teeth to said holder in a sliding manner.

6. The system of claim 5 wherein said mounting means includes frictional engaging means on said holder for engaging and retaining a support arm of said at least one of said shade and hue specimen teeth.

7. The system of claim 4 further comprising first and second support arms for respectively coupling a pair of said first and second shade and hue specimen teeth to a respective holder.

8. The system of claim 7 wherein each holder includes permanent affixing means for attaching said first support arm to a respective holder.

9. The system of claim 8 wherein each holder further includes first and second mounting studs respectively inserted in first and second apertures in said first and second support arms, and wherein an adhesive permanently attaches said first mounting stud to said first support arm and said second mounting stud is removably from said second aperture.

10. The system of claim 7 wherein each holder further includes snap-acting coupling means for removably attaching said second support arm to said holder.

11. The system of claim 1 further comprising a shade and hue reference guide having a plurality of reference teeth each having a difference shade and hue.

12. The system of claim 11 further comprising a plurality of shade and hue units, wherein each shade and hue unit include respective first and second shade and hue specimen teeth having the same shade and hue, and wherein the shade and hue of the specimen teeth of each shade and hue unit vary over a range of shades and hues.

13. The system of claim 12 wherein said shade and hue reference guide includes a first shade guide and a second hue guide, and wherein each of said first shade nd second hue guides includes a plurality of reference teeth having a difference shade and a different hue, respectively.

14. The system of claim 13 wherein said shade and hue reference guide further includes a panel having first and second sides, and wherein said first shade guide is disposed on the first side of said panel and said second hue guide is disposed on said second side of said panel.

15. The system of claim 14 further comprising a base including means for engaging and supporting said panel in a generally upright orientation.

16. The system of claim 15 wherein said means for engaging and supporting said panel includes an elongated, generally linear slot for receiving said panel.

17. The system of claim 16 wherein said base further include a plurality of support means for receiving and supporting said shade and hue units in a generally upright orientation, wherein each support means supports a group of shade and hue units having the same shade and hue.

18. The system of claim 17 wherein each of said support means includes a recessed compartment in said base having a plurality of spaced slots, and wherein each slot is adapted to engage a respective holder.

19. The system of claim 11 further comprising a base with a cover, wherein said base is adapted to receive and support said shade and hue reference guide and each of said shade and hue units in a generally upright orientation.

20. The system of claim 19 wherein said base further includes means for receiving and supporting a holder with a pair of specimen teeth tabs adapted for the fabrication of a pair of specimen teeth having a custom-made shade and hue.

21. A dental tooth shade and hue matching reference guide for matching the shade and hue of artificial teeth with the shade and hue of a patient's natural teeth or for providing artificial teeth with a life-like shade and hue, said reference guide comprising:
 a panel having first and second opposed sides, wherein said first and second opposed sides are provided with a solid color;
 a first plurality of reference teeth each having a difference shade, wherein said first plurality of teeth are disposed on said first side of said panel and arranged by shade; and
 a second plurality of reference teeth each having a difference hue, wherein said second plurality of teeth are disposed on said second side of said panel and arranged by hue.

22. The dental tooth shade and hue matching reference guide of claim 21 wherein said solid color is white, blue or neutral gray.

23. The dental tooth shade and hue matching reference guide of claim 21 wherein said first plurality of reference teeth are arranged by shade from light to dark and said second plurality of reference teeth are arranged by hue into a plurality of groups, with said second plurality of reference teeth arranged by shade within each of said groups.

24. The dental tooth shade and hue matching reference guide of claim 21 further comprising a plurality of support arms each coupling a respective one of said first or second pluralities of reference teeth to said panel.

25. The dental tooth shade and hue matching reference system for matching the shade and hue of artificial teeth with the shade and hue of a patient's natural teeth or for providing artificial teeth with a life-like shade and hue, said system comprising:
 a plurality of shade and hue units each having a difference shade/hue and covering a range of shades and hues of a patient's natural teeth or having a range of like-like shades and hues, wherein each shade and hue unit includes:
 a holder; and
 first and second shade and hue specimen teeth each having the same shade and hue, wherein at least one of said shade and hue specimen teeth is removably attached to said holder, and wherein said holder includes shade and hue identifying data and a patient identification area;

a shade and hue reference guide having a plurality of reference teeth each having a different shade and hue, said shade and hue reference guide including a first shade guide and a second hue guide, wherein each of said first shade and second hue guides includes a plurality of reference teeth having a difference shade and a different hue, respectively, and wherein said shade and hue reference guide includes a panel having first and second sides, with said first shade guide disposed on the first side of said panel and said second hue guide disposed on the second side of said panel; and a base with a removable cover for receiving and supporting said plurality of shade and hue units and said shade and hue reference guide.

26. A dental tooth shade and hue and size and shape matching reference system for matching the shade and hue and size and shape of artificial teeth with the shade and hue and size and shape of a patient's natural teeth or for providing artificial teeth with a life-like shade and hue and size and shape, said system comprising:

a shade and hue and size and shape unit having a shade and hue and size and shape of a patient's natural teeth or having a lifelike shade and hue and size and shape, size and shape, shade and hue and size and shape unit includes:

a holder; and first and second shade and hue and size and shape specimen teeth each having the same shade and hue and size and shape, wherein at least one of said shade and hue and size and shape specimen teeth includes a support arm sized to be easily handled by a thumb and forefinger grip of a user and removably attached to said holder, and characterized in that said holder includes shade and hue and size and shape identifying data for said specimen teeth and a patient identification area, and said support arm of said removably specimen tooth includes shade and hue and size and shape identifying data.

27. The system of claim 26 wherein each of said first and second shade and hue and size and shape specimen teeth further includes a tab coupled to a respective support arm and providing a base for building up a specimen tooth having a shade and hue and size and shape of a patient's natural teeth or a life-like shade and hue and size and shape.

28. The system of claim 27 wherein each specimen tooth is built up of a composite material to match the patient's natural teeth or life-like teeth.

29. The system of claim 27 wherein each specimen tooth is built up of a cold cure colored powder to match the patient's natural teeth or life-like teeth.

30. The system of claim 26 further comprising a plurality of shade and hue and size and shape units, wherein each shade and hue and size and shape unit includes respective first and second shade and hue and size and shape specimen teeth having the same shade and hue and size and shape, and wherein the shade and hue of the specimen teeth of each shade and hue and size and shape unit vary over a range of shades and hues.

31. The system of claim 30 wherein each holder comprises a generally flat panel adapted to receive and support a respective pair of first and second shade and hue and size and shape specimen teeth.

32. The system of claim 31 wherein each holder includes mounting means for removably coupling at least one of said shade and hue and size and shape specimen teeth to said holder.

33. The system of claim 32 wherein each of said mounting means couples at least one of said shade and hue and size and shape specimen teeth to said holder in a sliding manner.

34. The system of claim 32 wherein said mounting means includes frictional engaging means on said holder for engaging and retaining a support arm of said at least one of said shade and hue and size and shape specimen teeth.

35. The system of claim 26 further comprising first and second support arms for respectively coupling a pair of said first and second shade and hue and size and shape specimen teeth to a respective holder.

36. The system of claim 35 wherein each holder includes permanent affixing means for attaching said first support arm to a respective holder.

37. The system of claim 36 wherein each holder further includes first and second mounting studs respectively inserted in first and second apertures in said first and second support arms, and wherein an adhesive permanently attaches said first mounting stud to said first support arm and said second mounting stud is removably from said second aperture.

38. The system of claim 37 wherein each holder further includes snap-acting coupling means for removably attaching said second support arm to said holder.

39. The system of claim 26 further comprising a shade and hue reference guide having a plurality of reference teeth each having a difference shade and hue.

40. The system of claim 39 further comprising a plurality of shade and hue and size and shape units, wherein each shade and hue and size and shape unit includes respective first and second shade and hue and size and shape specimen teeth having the same shade and hue and size and shape, and wherein the shade and hue of the specimen teeth of each shade and hue unit vary over a range of shades and hues.

41. The system of claim 39 wherein said shade and hue reference guide includes a first shade guide and a second hue guide, and wherein each of said first shade and second hue guides includes a plurality of reference teeth having a difference shade and a different hue, respectively.

42. The system of claim 41 wherein said shade and hue reference guide further includes a panel having first and second sides, and wherein said first shade guide is disposed on the first side of said panel and said second hue guide is disposed on said second side of said panel.

43. The system of claim 42 further comprising a base including means for engaging and supporting said panel in a generally upright orientation.

44. The system of claim 43 wherein said means for engaging and supporting said panel includes an elongated, generally linear slot for receiving said panel.

45. The system of claim 44 wherein said base further includes a plurality of support means for receiving and supporting said shade and hue and size and shape units in a generally upright orientation, wherein each support means supports a group of shade and hue and size and shape units having the same shade and hue.

46. The system of claim 45 wherein each of said support means includes a recessed compartment in said base having a plurality of spaced slots, wherein each slot is adapted to engage a respective holder.

47. The system of claim 39 further comprising a base with a cover, wherein said base is adapted to receive and support said shade and hue reference guide and each of said shade and hue and size and shape units in a generally upright orientation.

* * * * *

UNITED STATES PATENT AND TRADEMARK OFFICE
CERTIFICATE OF CORRECTION

PATENT NO. : 5,257,931

DATED : November 2, 1993

INVENTOR(S) : Bruno Pozzi

It is certified that error appears in the above-identified patent and that said Letters Patent is hereby corrected as shown below:

Col. 2, line 1, after "holder" insert --10.--

Col. 6, line 28, after "shade" insert --and hue--.

Col 8, line 64 "said" should be --sized--.

Col. 9, line 36, "removably" should be --removable--; line 46, "include" should be --includes--; and line 54, "nd" should be --and--.

Col. 10, line 2 "include" should be --includes--; line 29, "difference" should be --different--; line 34, "difference" should be --different--; and line 56, "difference" should be --different--.

Col. 11, line 24, "lifelike" should be --life-like--; line 26, delete the second "size and shape" and insert --wherein said--; and line 38, "removably" should be --removable--.

Col. 12, line 22, "removably" should be --removable--; line 29, "difference" should be --different--; line 42, "difference" should be --different--; and line 63, after "slots", insert --and--.

Signed and Sealed this

Sixteenth Day of August, 1994

Attest:

BRUCE LEHMAN

Attesting Officer

Commissioner of Patents and Trademarks